(12) United States Patent
Lee et al.

(10) Patent No.: US 7,943,088 B2
(45) Date of Patent: May 17, 2011

(54) BIOCHEMICAL ANALYZER AND METHOD OF CONTROLLING INTERNAL TEMPERATURE OF THE BIOCHEMICAL ANALYZER

(75) Inventors: Jeong-gun Lee, Seoul (KR); Yong-moo Shin, Seongnam-si (KR); Kui-hyun Kim, Seoul (KR); Jin-han Chung, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 517 days.

(21) Appl. No.: 11/972,708

(22) Filed: Jan. 11, 2008

(65) Prior Publication Data

US 2009/0022625 A1 Jan. 22, 2009

(30) Foreign Application Priority Data

Jul. 19, 2007 (KR) .................. 10-2007-0072488

(51) Int. Cl.
*C12Q 1/68* (2006.01)
*G01N 15/06* (2006.01)
(52) U.S. Cl. ............. 422/50; 422/68.1; 422/62; 422/63; 422/55; 422/58; 436/43
(58) Field of Classification Search .................... 422/50, 422/68.1, 62, 63
See application file for complete search history.

(56) References Cited

U.S. PATENT DOCUMENTS

| | | | | |
|---|---|---|---|---|
| 5,876,675 A * | 3/1999 | Kennedy | .......................... | 422/99 |
| 6,132,685 A * | 10/2000 | Kercso et al. | .................. | 422/104 |
| 6,900,889 B2 * | 5/2005 | Bjornson et al. | .............. | 356/246 |
| 6,986,837 B2 * | 1/2006 | Chow et al. | .................... | 204/603 |
| 7,223,949 B2 * | 5/2007 | Deka et al. | .................... | 219/548 |
| 7,465,545 B2 * | 12/2008 | Kim et al. | .......................... | 435/6 |
| 2008/0056949 A1 * | 3/2008 | Lee et al. | ......................... | 422/72 |
| 2008/0226502 A1 * | 9/2008 | Jonsmann et al. | ........... | 422/68.1 |

* cited by examiner

*Primary Examiner* — Brian J Sines
(74) *Attorney, Agent, or Firm* — Sughrue Mion, PLLC

(57) ABSTRACT

Provided is a biochemical analyzer in which a microfluidic biochemical assay may be performed. The analyzer includes: a microfluidic device loading space including a microfluidic device supporting unit detachably supporting a microfluidic device including an energy application region in which an energy is applied; an energy source loading space including an energy source applying the energy to the radiation application region; and an isolation wall isolating the microfluidic device loading space and the energy source loading space to prevent heat transfer between the microfluidic device loading space and the energy source loading space and including a window through which the energy can be transmitted. A method of controlling an internal temperature of the biochemical analyzer is also provided.

19 Claims, 5 Drawing Sheets

BIOCHEMICAL ANALYZER AND METHOD OF CONTROLLING INTERNAL TEMPERATURE OF THE BIOCHEMICAL ANALYZER

CROSS-REFERENCE TO RELATED PATENT APPLICATION

This application claims priority from Korean Patent Application No. 10-2007-0072488, filed on Jul. 19, 2007, in the Korean Intellectual Property Office, the disclosure of which is incorporated herein in its entirety by reference.

BACKGROUND OF THE INVENTION

1. Field of the Invention

The present invention relates to the field of biochemistry, and more particularly, to a biochemical analyzer which performs various assays of biological samples and to a method of controlling the internal temperature of the biochemical analyzer.

2. Description of the Related Art

Recently, a biochemical assay technique to diagnose a disease or detect the presence of a cellular component from a trace amount of a fluid sample such as blood or urine is advancing. A microfluidic device that is used in a biochemical assay of a trace amount of a fluid generally includes a chamber containing the fluid, a channel through which the fluid flows, and a valve controlling the flow of the fluid. A device in which an assay including a biochemical reaction is performed on a microchip is called a "biochip". In particular, a device designed for performing various steps of fluid treatments and manipulations on a single chip is called a "lab-on-a-chip".

In order to move a fluid in a microfluidic device, a driving pressure is required. The driving pressure may be a capillary pressure or a pressure exerted by a separate pump. Disk type microfluidic devices including a chamber and a channel have recently been proposed, and a fluid movement is caused by a centrifugal force generated by rotating the disk type microfluidic devices. These disk type microfluidic devices are also called as "Lab CDs" or "Lab-on-a-CDs".

An apparatus configured to provide atmospheric conditions suitable for a measurable biological sample reaction and to detect the reaction results is designated as a "biochemical analyzer". Meanwhile, in some cases, in order to perform a reaction such as a lysis reaction or to open or close a valve controlling a fluid flow, an energy application is needed. The energy application may be electromagnetic radiation such as laser. For the electromagnetic radiation application, a biochemical analyzer should include an energy source including a laser diode (LD) or the like.

FIGS. 1A and 1B are graphs illustrating the characteristics of a laser diode, specifically the characteristics of a currently commercially available model (Sony SLD 323V) which is a laser diode. Referring to FIGS. 1A and 1B, as an external temperature (Tc) increases, the optical intensity and wavelength of the laser diode increase. In most other laser diodes, in addition to the model Sony SLD 323V, an optimal optical intensity and wavelength for performing a biochemical reaction using a biological sample are achieved at about 25° C.

However, optimal results of a biochemical assay of a biological sample, which is originated from human beings, are achieved at about 36.5-37.5° C. which is similar to the normal body temperature of most people. As such, since the optimal operational temperature condition of an energy source is different from the optimal temperature condition of a biochemical assay of a biological sample, the accuracy of the results of the assays is lowered, and energy consumption for the assays is increased.

SUMMARY OF THE INVENTION

The present invention provides a biochemical analyzer that can simultaneously satisfy the optimal operational temperature condition of an energy source and the optimal temperature condition for a biochemical assay of a biological sample, and a method of controlling the internal temperature of the biochemical analyzer.

According to an aspect of the present invention, there is provided a biochemical analyzer including: a microfluidic device loading space which receives a microfluidic device, the microfluidic device loading space including a microfluidic device supporting unit detachably supporting the microfluidic device, wherein the microfluidic device includes an energy application region to which an energy is applied; an energy source loading space which receives an energy source, the energy source applying the energy to the energy application region of the microfluidic device; and an isolation wall isolating the microfluidic device loading space from the energy source loading space to prevent heat transfer between the microfluidic device loading space and the energy source loading space, the isolation wall includes a window through which the energy can be transmitted.

The microfluidic device supporting unit may include a motor rotating the microfluidic device.

The energy source may include a laser diode (LD).

The biochemical analyzer may further include an energy source movement unit horizontally moving the energy source.

The microfluidic device loading space may further include a heater for heating the microfluidic device.

The microfluidic device loading space may further include a first temperature sensor for measuring a temperature of the microfluidic device loading space, and if a temperature measured by the first temperature sensor is lower than a first reference temperature, the heater may be operated.

The first reference temperature may be about 36- about 38° C. according to one embodiment of the present application. According to another embodiment, the first reference temperature may be about 37° C.

The biochemical analyzer may further includes a first cooler for lowering the temperature of the microfluidic device loading space, and if the temperature measured by the first temperature sensor is higher than the first reference temperature, the first cooler may be operated.

The first cooler may include an inlet fan for inducing external air to flow into the microfluidic device loading space.

The first cooler may further include a filter for filtering particles contained in the external air entering into the microfluidic device loading space.

The biochemical analyzer may further include a second cooler for lowering the temperature of the energy source loading space.

The energy source loading space may further include a second temperature sensor for measuring the temperature of the energy source loading space, and if a temperature measured by the second temperature sensor is higher than a second reference temperature, the second cooler may be operated.

The second cooler may include an energy source cooling fan for cooling the energy source by inducing external air to flow into the energy source loading space.

The second cooler may include an energy source cooling duct for guiding the external air into the energy source.

The second reference temperature may be about 24- about 26° C. according to one embodiment of the present application. In another embodiment, the temperature may be about 25° C.

The isolation wall except at least the window may be formed of a plastic material.

The window may be formed of glass, crystal, or plastic.

Anti-reflect coating may be applied to a surface of the window.

According to another aspect of the present invention, there is provided a method of controlling an internal temperature of the biochemical analyzer. The method includes measuring a temperature of the microfluidic device loading space using the first temperature sensor; and operating the heater if the measured temperature is lower than a first reference temperature. The method includes measuring the temperature of the energy source loading space using the second temperature sensor; and operating the second cooler if the measured temperature is higher than a second reference temperature. This can be achieved by a temperature controlling method which is known to one of ordinary skill in the art, e.g., a PID control technique.

In the method of controlling the internal temperature of the biochemical analyzer, if the temperature measured by the first temperature sensor is higher than the first reference temperature, the first cooler may be operated. This can be achieved by a temperature controlling method which is known to one of ordinary skill in the art, e.g., a PID control technique.

According to a biochemical analyzer of the present invention, the optimal operational temperature condition of an energy source and the optimal reaction temperature condition for a biochemical assay of a biological sample can be satisfied at the same time even when the above two conditions are different. Therefore, the accuracy and reliability of the assays of a biochemical analyzer can be enhanced, and energy consumption for the assays can be reduced.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

A biochemical analyzer and a method of controlling the internal temperature of the biochemical analyzer according to the present invention will now be described more fully with reference to the accompanying drawings, in which exemplary embodiments of the invention are shown.

Figures 1A, 1B:
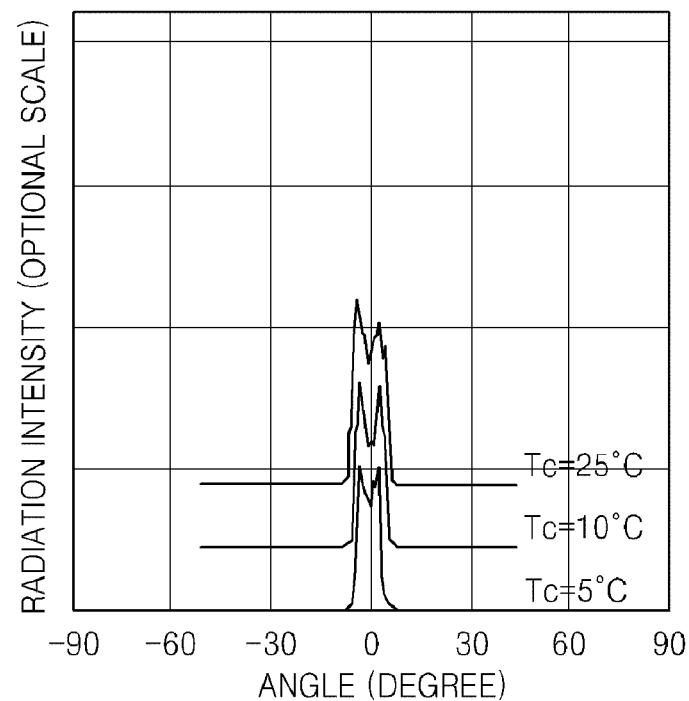
FIGS. 1A and 1B are graphs illustrating the characteristics of a laser diode.
Figure 2:
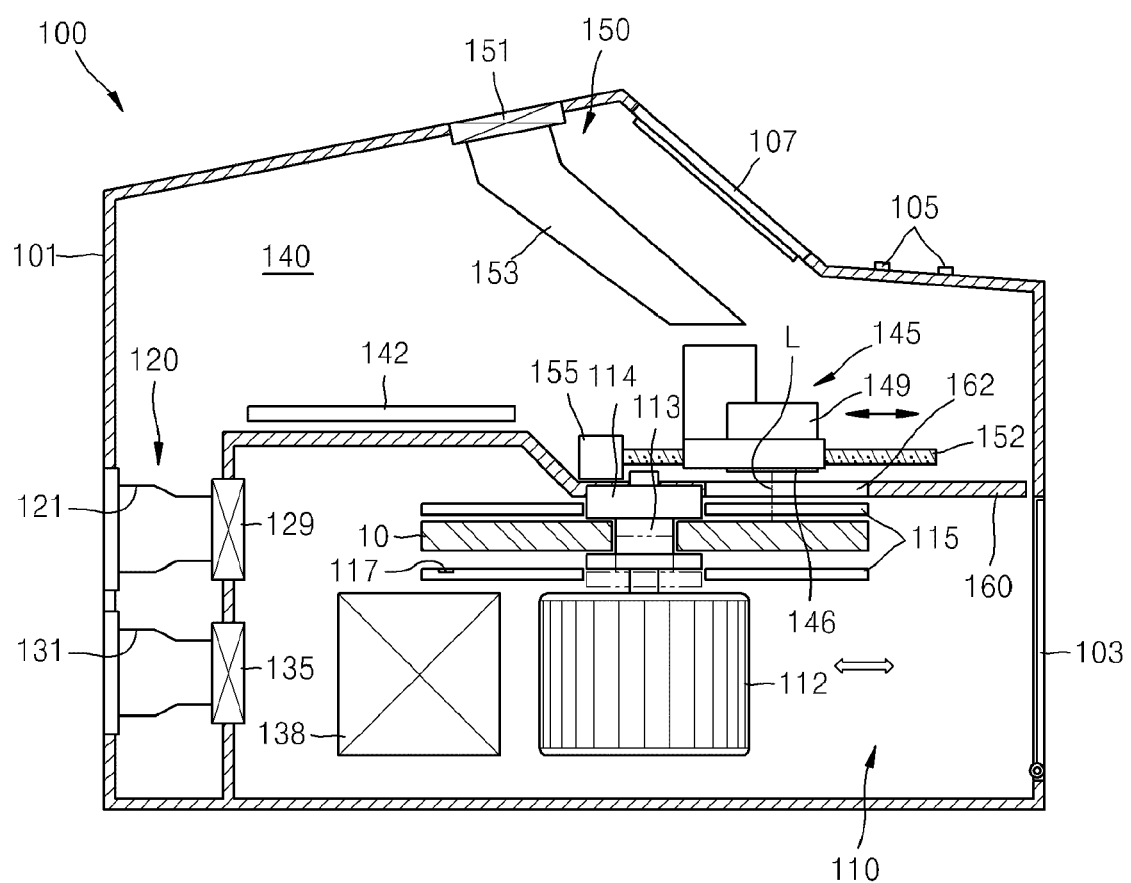
FIG. 2 is a schematic sectional view illustrating a biochemical analyzer according to an exemplary embodiment of the present invention.
Figure 3:
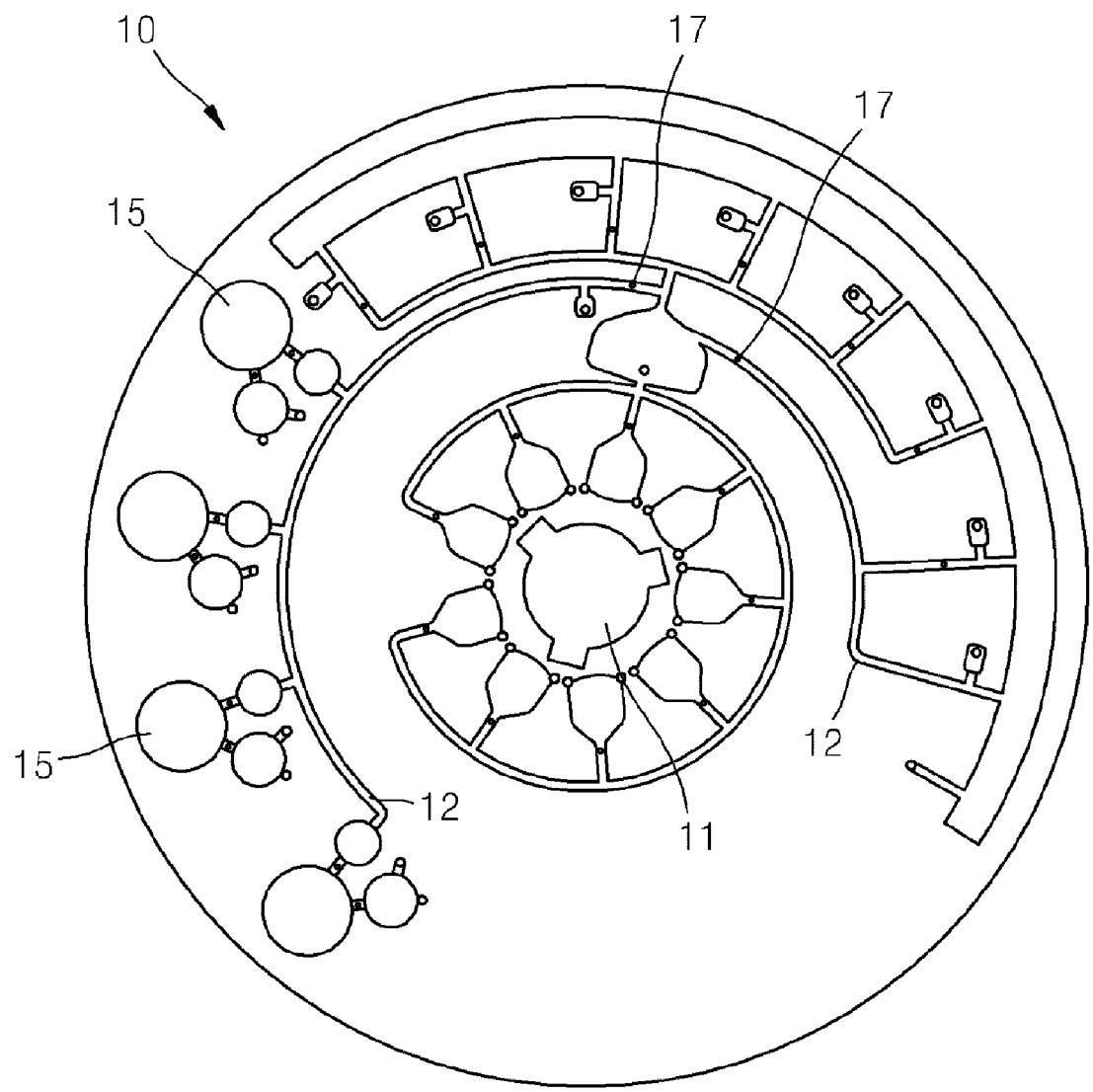
FIG. 3 is a plan view illustrating an example of a microfluidic device which can be loaded in the biochemical analyzer of FIG. 2.
Figure 4:
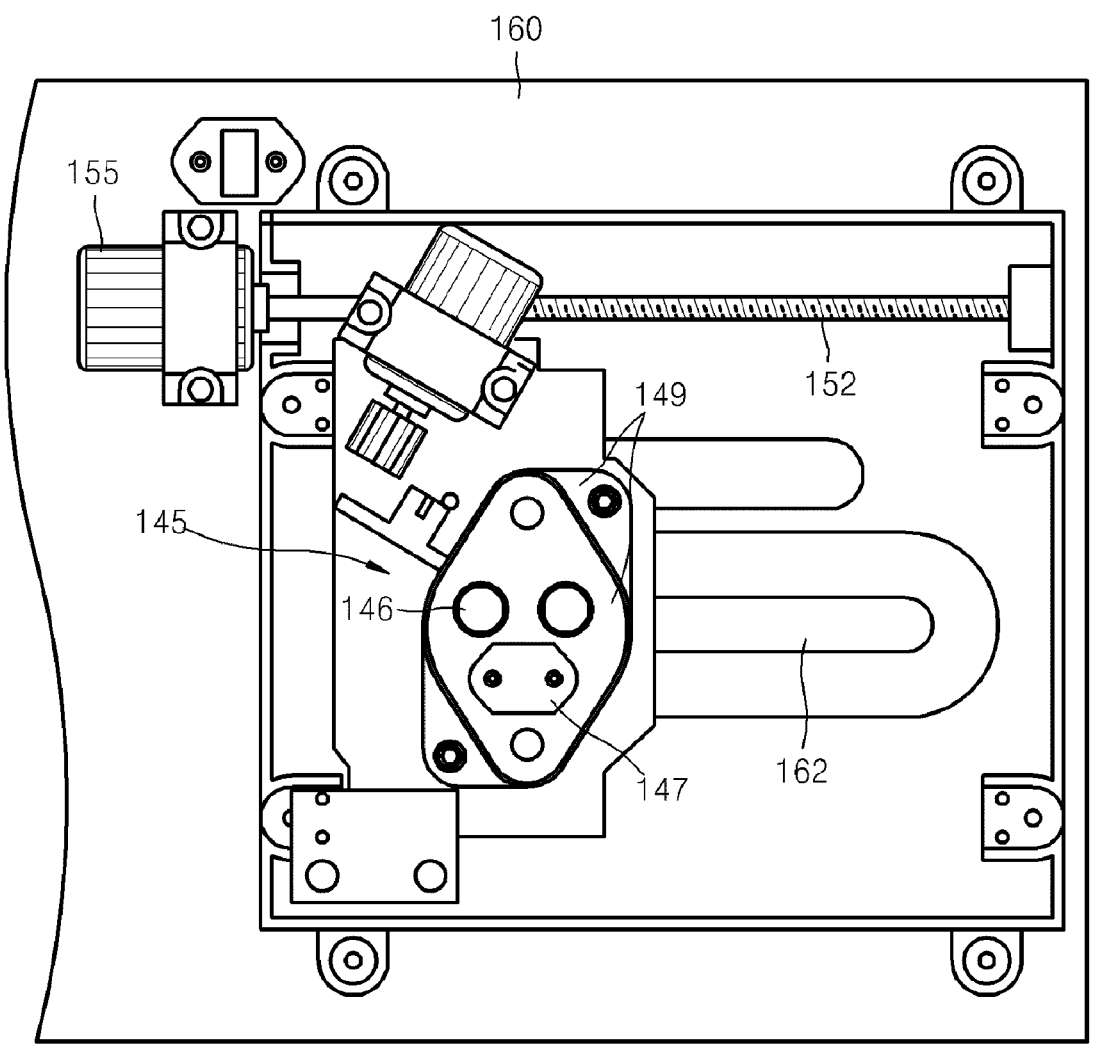
FIG. 4 is a plan view illustrating the inside of an energy source loading space of FIG. 2.
Figure 5:
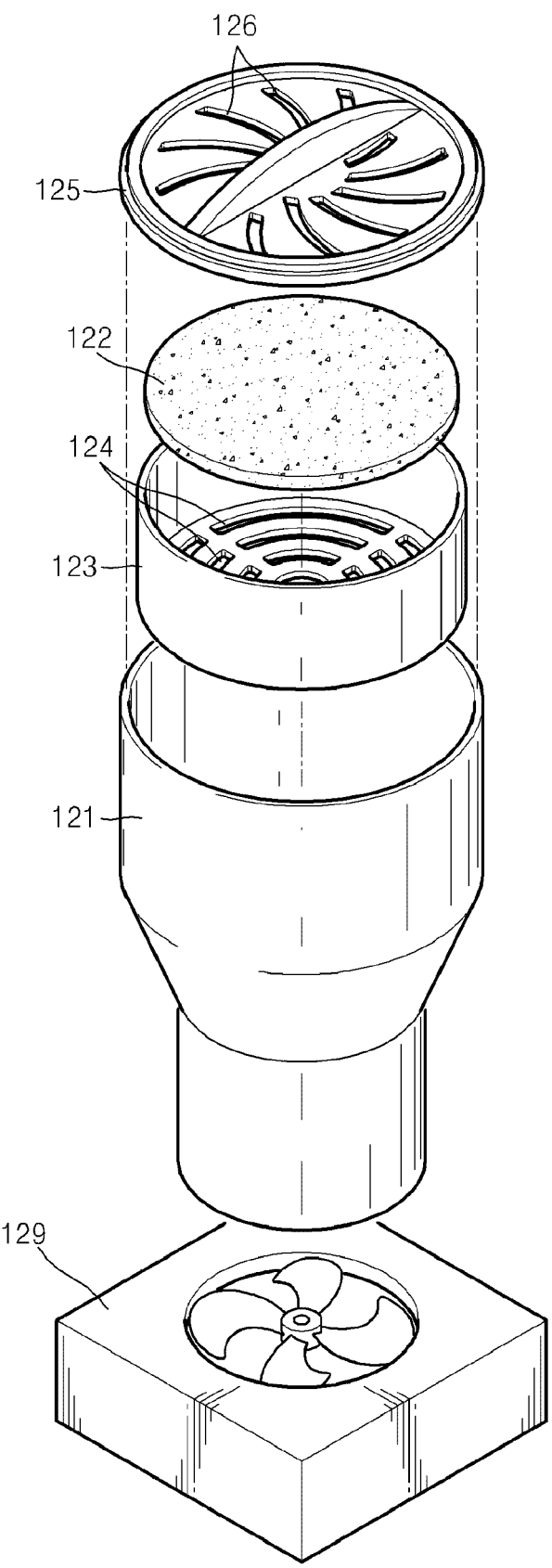
FIG. 5 is an exploded perspective view illustrating an inlet duct of FIG. 2.

FIG. 2 is a schematic sectional view illustrating a biochemical analyzer according to an exemplary embodiment of the present invention, FIG. 3 is a plan view illustrating an example of a microfluidic device which can be loaded in the biochemical analyzer of FIG. 2, FIG. 4 is a plan view illustrating the inside of an energy source loading space of FIG. 2, and FIG. 5 is an exploded perspective view illustrating an inlet duct of FIG. 2.

Referring to FIG. 2, a biochemical analyzer 100 according to an exemplary embodiment of the present invention includes, in a case 101, a microfluidic device loading space 110, an energy source loading space 140, and an isolation wall 160 isolating the two spaces 110 and 140. The microfluidic loading space 110 includes a microfluidic device supporting unit for detachably supporting a microfluidic device 10. The case 101 includes an input unit 105 including keys for inputting a command, etc., a display unit including an LCD panel for displaying an operating state of the biochemical analyzer 100, etc., and a front door 103.

Referring to FIG. 3, the microfluidic device 10 is structured such that a desired assay reaction of a biological sample (e.g., blood) can be performed in a disk type platform. The microfluidic device 10 includes a chamber 15 to receive a fluid, a channel 12 for providing the path of the fluid, and a valve 17 for controlling the flow of the fluid in the channel 12. A center portion of the microfluidic device 10 includes a spindle insertion hole 11 for inserting a spindle 113 (see FIG. 2) as will be described later.

The microfluidic device 10 may be formed of a plastic material which has good formability, is optically transparent, and has a biologically inactive surface, e.g., PMMA (polymethyl methacrylate), PDMS (polydimethylsiloxane), or PC (polycarbonate). However, a material of the microfluidic device 10 is not limited to the above-described examples provided that it is a material having chemical and biological stability, optical transparency, and mechanical processability. The platform of the microfluidic device 10 may be formed of multi-layered plates. A space and a path respectively corresponding to the chamber 15 and the channel 12 can be provided in the platform by forming engraved structures corresponding to the chamber 15 and the channel 12 in facing surfaces of plates and joining the plates. The joining of the plates can be achieved by various methods including, but not limited to, an adhesion using an adhesive or a double-sided adhesive tape, ultrasonic fusion, laser welding, or adhesion using a UV adhesive.

In order to perform a desired reaction such as a lysis reaction, electromagnetic radiation such as laser is applied to cells in a sample. In this case, the chamber 15 wherein the specific reaction occurs serves as an electromagnetic radiation application region wherein electromagnetic energy is applied. On the other hand, when the valve 17 is formed of a composition including a phase transition material and a plurality of metal oxide particles, the channel 12 can be opened by applying electromagnetic radiation (e.g., laser) to the valve 17. In this case, the valve 17 serves as an electromagnetic radiation application region wherein electromagnetic energy is applied.

Referring again to FIG. 2, the microfluidic device supporting unit included in the microfluidic device loading space 110 includes the spindle 113 inserted into the spindle insertion hole 11 (see FIG. 3), a microfluidic device driving motor 112 rotating the microfluidic device 10 by rotating the spindle 113, and a clamp 114 pressing the microfluidic device 10 inserted into the spindle 113 to prevent the separation of the microfluidic device 10 from the spindle 113. The clamp 114 can be fastened to the isolation wall 160.

The spindle 113 moves in a restricted manner toward the microfluidic device driving motor 112, as shown by a double dashed line. The microfluidic device driving motor 112 is horizontally reciprocally moved so that it can be moved out of the front door 103 of the case 101. When an appropriate command is given through the input unit 105, the front door 103 is opened and the microfluidic device driving motor 112 is moved out of the case 101 in a manner wherein the spindle 113 is constricted toward the microfluidic device driving motor 112, thereby enabling easy insertion of the microfluidic device 10 into the spindle 113. Then, when another appropriate command is given into the input unit 105, the microfluidic device driving motor 112 is returned to the microfluidic device loading space 110, the spindle 113 is moved upward and connected to the clamp 114 so that the microfluidic device 10 is not separated from but is fastened to the spindle 113, and the front door 103 is closed. While the spindle 113 is rotated, a centrifugal force is exerted to the microfluidic device 10. The centrifugal force may be at least one of external conditions for inducing a specific reaction in a sample contained in the microfluidic device 10. In the embodiment shown in FIGS. 2 and 3, the microfluidic device 10 has a disk shape, and the spindle 113 connected to the microfluidic device driving motor 112 rotatably supports the microfluidic device 10. However, the present invention is not limited thereto. For example, a biochemical analyzer including a table simply supporting a chip type microfluidic device is also within the scope of the present invention.

The microfluidic device loading space 110 includes a heater 115 for heating the microfluidic device 10. In order to efficiently heat the microfluidic device 10, the heater 115 is disposed to be close to the upper and lower surfaces of the microfluidic device 10. The heater 115 may be any of various types of heaters, e.g., a resistor or a halogen lamp. In the microfluidic device loading space 110, a first temperature sensor 117 for measuring the internal temperature of the microfluidic device loading space 110 is disposed adjacent to the microfluidic device 10. The embodiment shown in FIGS. 2 and 3 illustrates that the heater 115 and the first temperature sensor 117 are disposed adjacent to the microfluidic device 10. However, the present invention is not limited thereto provided that the heater 115 and the first temperature sensor 117 are structured such that the microfluidic device loading space 110 is heated and the internal temperature of the microfluidic device loading space 110 can be measured.

The biochemical analyzer 100 includes a first cooler 120 for cooling the inside of the microfluidic device loading space 110. The first cooler 120 includes an inlet fan 129 for forcibly inducing external air to flow into the microfluidic device loading space 110, and an inlet duct 121 for guiding the external air into the microfluidic device loading space 110. The first cooler 120 also includes an outlet fan 135 for forcibly discharging air from the microfluidic device loading space 110 and an outlet duct 131 for guiding the internal air outward. FIG. 2 illustrates that the first cooler 120 includes the inlet fan 129 and the outlet fan 135, but the present invention is not limited thereto. For example, a biochemical analyzer in which a thermoelectric cooler is included in a microfluidic device loading space is also within the scope of the present invention.

Referring to FIG. 5, the inlet duct 121 includes a filter 122 for filtering particles (e.g., dust) included in external air entering into the microfluidic device loading space 110 (see FIG. 2). The filter 122 is received in a filter case 123 having slits 124 and inserted into the inlet duct 121. In order to prevent the separation of the filter 122 from the inlet duct 121, a detachable cap 125 is provided at an entrance of the inlet duct 121. External air enters into the inlet duct 121 via slits 126 formed in the cap 125.

The microfluidic device loading space 110 includes an optical detector 138 for determining the presence and amount of a desired or target component by optically detecting a reaction occurred in a sample of the microfluidic device 10. The optical detector 138 determines the presence and amount of a desired or target component by measuring the absorbance or fluorescence intensity of a product of the reaction occurred in the sample contained in the chamber 15 (see FIG. 3).

The energy source loading space 140 includes an energy source 145 applying electromagnetic energy to an electromagnetic radiation application region of the microfluidic device 10. The energy source 145 includes a laser diode 146 applying laser L, which is a kind of electromagnetic radiation, to the microfluidic device 10 and a heat sink 149 for heat radiation. A second temperature sensor 147 (see FIG. 4) for measuring the internal temperature of the energy source loading space 140 is disposed in the energy source 145.

The biochemical analyzer 100 further includes an energy source movement unit for horizontally moving the energy source 145 along a lengthwise direction of a transparent window 162 formed in the isolation wall 160. Referring to FIG. 4, the energy source movement unit includes an energy source movement motor 155 and a helical shaft 152 coaxially connected to a shaft of the energy source moving motor 155. The helical shaft 152 includes a helical gear, and thus, is engaged with the energy source 145. Thus, the energy source 145 can be reciprocally moved in the lengthwise direction of the window 162, which may be transparent, according to the rotation direction of the helical shaft 152.

Referring again to FIG. 2, the biochemical analyzer 100 includes a second cooler 150 for cooling the inside of the energy source loading space 140. The second cooler 150 includes an energy source cooling fan 151 for inducing external air to flow into the energy source loading space 140 and an energy source cooling duct 153 which extends to be close to the energy source 145 and guides the external air into the energy source 145. FIG. 2 illustrates that the second cooler 150 includes the energy source cooling fan 151, but the present invention is not limited thereto. For example, a biochemical analyzer wherein a thermoelectric cooler is included in an energy source loading space is also within the scope of the present invention.

The isolation wall 160 (except for at least the window 162) isolating the microfluidic device loading space 110 and the energy source loading space 140 may be formed of a plastic which prevents heat transfer between the two spaces 110 and 140 and which is inexpensive. The transparent window 162 may be formed of glass, crystal, or plastic which is transparent with respect to the laser L emitted from the laser diode 146. According to an exemplary embodiment of the present invention, anti-reflect coating may be applied to a surface of the transparent window 162 in order to enhance transparency.

The biochemical analyzer 100 includes a main circuit board 142. The main circuit board 142 functions to control the internal temperature of the biochemical analyzer 100, to control the driving of the motors 112 and 150 and the light emission of the laser diode 146, and to assay a sample reaction using the optical detector 138.

Hereinafter, a method of controlling the internal temperature of the biochemical analyzer 100 will be described with reference to FIG. 2. The temperature of the microfluidic device loading space 110 and the temperature of the energy source loading space 140 are independently controlled. A temperature control of the microfluidic device loading space 110 is performed as follows. While the biochemical analyzer 100 is operating, the temperature of the microfluidic device loading space 110 is periodically measured using the first temperature sensor 117. If the measured temperature is lower than a first reference temperature, the heater 115 is operated to increase the temperature of the microfluidic device loading space 110.

According to an exemplary embodiment of the present invention, the first reference temperature may be about 36° C. ☐ bout 38° C. In one embodiment, the first temperature may be about 37° C. which is known to be a temperature at which an optimal reaction result using a biological sample is achieved. Meanwhile, if a temperature measured by the first temperature sensor 117 is higher than the first reference temperature, the operation of the heater 115 is stopped, and the inlet and outlet fans 129 and 135 of the first cooler 120 are operated to lower the temperature of the microfluidic device loading space 110.

A temperature control of the energy source loading space 140 is performed as follows. While the biochemical analyzer 100 is operated, the temperature of the energy source loading space 140 is periodically measured using the second temperature sensor 147 (see FIG. 4). If the measured temperature is higher than a second reference temperature, the cooling fan 151 of the second cooler 150 is operated to lower the temperature of the energy source loading space 140. This can be achieved by a temperature control method obvious to one of ordinary skill in the art, e.g., a PID (proportional-integral-derivative) control technique.

According to an exemplary embodiment of the present invention, the second reference temperature may be 25° C. which is known to be a temperature at which light emitted from the laser diode 146 has an optimal optical intensity and wavelength.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A biochemical analyzer comprising:
   a microfluidic device loading space which receives a microfluidic device, the microfluidic device loading space comprising a microfluidic device supporting unit detachably supporting the microfluidic device;
   an energy source loading space which receives an energy source, the energy source applying the energy to the microfluidic device
   an isolation wall isolating the microfluidic device loading space from the energy source loading space to prevent heat transfer between the microfluidic device loading space and the energy source loading space, the isolation wall comprises a window through which the energy can be transmitted; and
   an optical detector which optically detects a reaction in the microfluidic device.

2. The biochemical analyzer of claim 1, wherein the microfluidic device supporting unit comprises a motor which rotates the microfluidic device.

3. The biochemical analyzer of claim 1, wherein the energy source comprises a laser diode (LD).

4. The biochemical analyzer of claim 3, further comprising an energy source movement unit which horizontally moves the energy source.

5. The biochemical analyzer of claim 1, wherein the microfluidic device loading space further comprises a heater for heating the microfluidic device.

6. The biochemical analyzer of claim 5, wherein the microfluidic device loading space further comprises a first temperature sensor for measuring a temperature of the microfluidic device loading space, and
   wherein the heater is operated, if a temperature measured by the first temperature sensor is lower than a first reference temperature.

7. The biochemical analyzer of claim 6, wherein the first reference temperature is about from 36° C. to about 38° C.

8. The biochemical analyzer of claim 6, further comprising a first cooler for lowering the temperature of the microfluidic device loading space,
   wherein the first cooler is operated, if the temperature measured by the first temperature sensor is higher than the first reference temperature.

9. The biochemical analyzer of claim 8, wherein the first cooler comprises an inlet fan for inducing external air to flow into the microfluidic device loading space.

10. The biochemical analyzer of claim 9, wherein the first cooler further comprises a filter for filtering particles contained in the external air entering into the microfluidic device loading space.

11. The biochemical analyzer of claim 1, further comprising a second cooler for lowering the temperature of the energy source loading space.

12. The biochemical analyzer of claim 11, wherein the energy source loading space further comprises a second temperature sensor for measuring the temperature of the energy source loading space, and
   wherein the second cooler is operated, if a temperature measured by the second temperature sensor is higher than a second reference temperature.

13. The biochemical analyzer of claim 12, wherein the second cooler comprises an energy source cooling fan for lowering the temperature of the energy source by inducing external air to flow into the energy source loading space.

14. The biochemical analyzer of claim 13, wherein the second cooler comprises an energy source cooling duct for guiding the external air into the energy source.

15. The biochemical analyzer of claim 12, wherein the second reference temperature is about 25° C.

16. The biochemical analyzer of claim 1, wherein the isolation wall except at least the window is formed of a plastic material.

17. The biochemical analyzer of claim 1, wherein the window is formed of a glass, crystal, or plastic.

18. The biochemical analyzer of claim 17, wherein anti-reflect coating is applied to a surface of the window.

19. A biochemical analyzer comprising:
   a microfluidic device loading space which receives a microfluidic device, the microfluidic device loading space comprising a microfluidic device supporting unit detachably supporting the microfluidic device;
   an energy source loading space which receives an energy source, the energy source applying the energy to the microfluidic device
   a wall isolating the microfluidic device loading space from the energy source loading space to prevent heat transfer between the microfluidic device loading space and the energy source loading space, the wall comprises a window through which the energy can be transmitted; and
   an optical detector which optically detects a reaction in the microfluidic device.

* * * * *